United States Patent [19]

Schuler et al.

[11] 3,972,418
[45] Aug. 3, 1976

[54] MOLDED SUTURE PACKAGE

[75] Inventors: Michael Schuler, Piscataway;
Eberhard H. Thyen, Middlesex,
both of N.J.

[73] Assignee: Ethicon, Inc., Somerville, N.J.

[22] Filed: Nov. 25, 1974

[21] Appl. No.: 526,551

[52] U.S. Cl. .............................. 206/63.3; 206/227;
206/339; 206/382
[51] Int. Cl.² ........................................ A61L 17/02
[58] Field of Search .................. 206/63.3, 388, 227,
206/339, 348, 370, 380, 382

[56] References Cited
UNITED STATES PATENTS

| | | | |
|---|---|---|---|
| 3,112,825 | 12/1963 | Hammond et al. | 206/63.3 |
| 3,301,393 | 1/1967 | Regan, Jr. et al. | 206/63.3 |
| 3,338,401 | 8/1967 | Regan, Jr. | 206/63.3 |
| 3,376,973 | 4/1968 | Granowitz et al. | 206/63.3 |
| 3,545,608 | 12/1970 | Berger et al. | 206/63.3 |
| 3,613,879 | 10/1971 | Kemble | 206/63.3 |
| 3,648,949 | 3/1972 | Berger et al. | 206/227 |
| 3,749,238 | 7/1973 | Taylor | 206/227 |

*Primary Examiner*—William Price
*Assistant Examiner*—Bruce H. Bernstel
*Attorney, Agent, or Firm*—W. R. Eberhardt

[57] ABSTRACT

A laminated molded sterilizable package for sutures is constructed of a first molded sheet and a second cover sheet. The molded sheet has a centrally located needle chamber recess and a long, narrow suture channel extending outward of and in a generally spiral path around the needle chamber. In a preferred embodiment, the suture channel is characterized by having at least one curve in a reverse direction from the general direction of the spiral. The package is opened by peeling a portion of the cover sheet from the molded sheet to uncover the needle chamber and an adjacent length of the suture channel. The package is suitable for use with heavy denier monofilament sutures which may be withdrawn from the package singly or in groups. Sutures delivered from the package are characterized by having only gentle bends with no loops or coils and are suitable for use with little or no further straightening.

16 Claims, 18 Drawing Figures

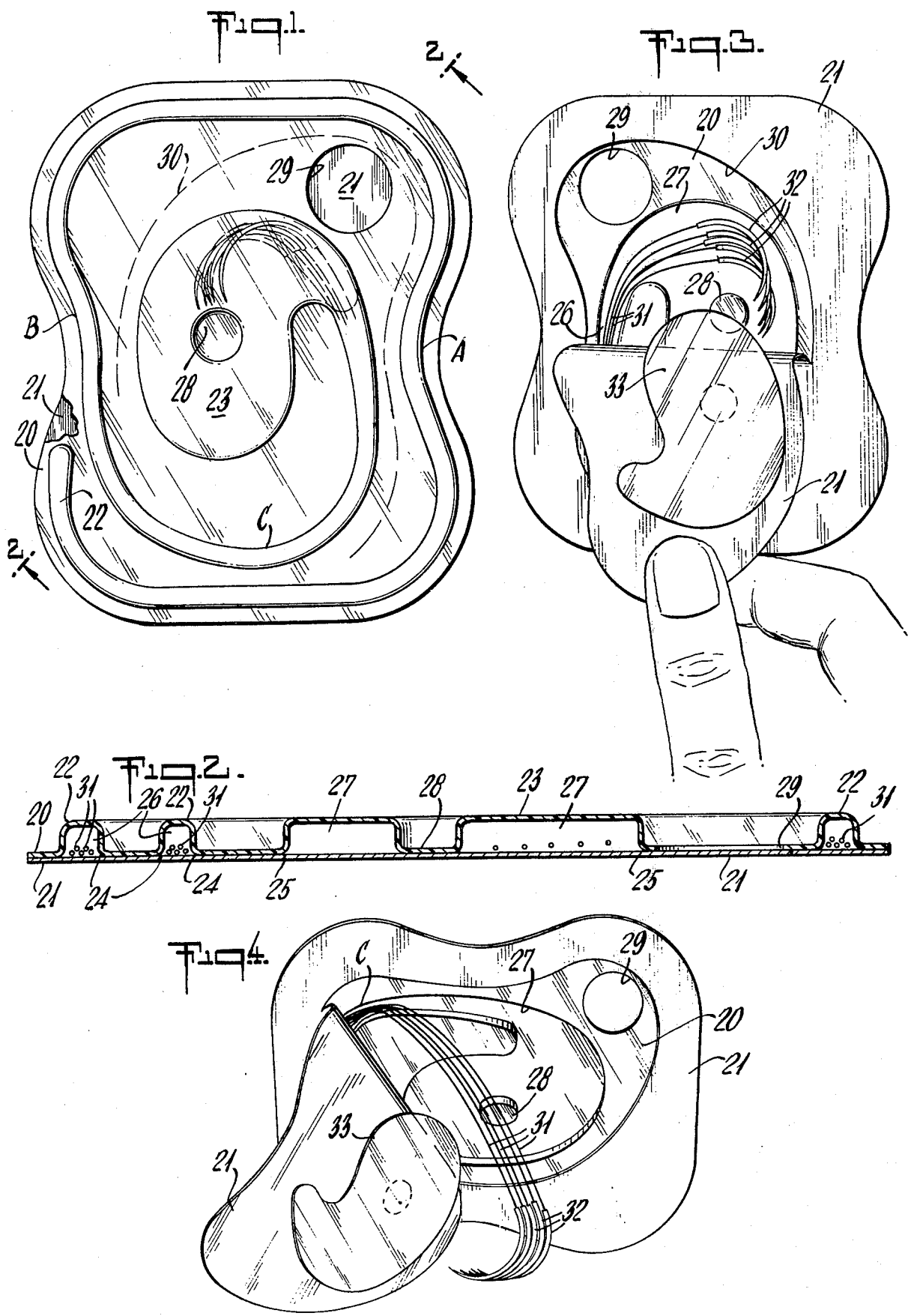

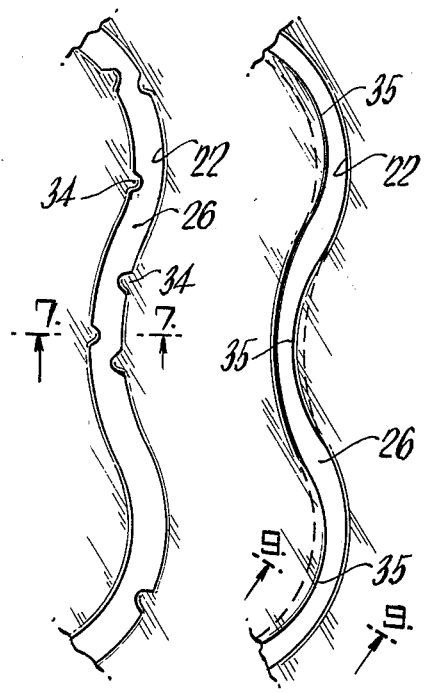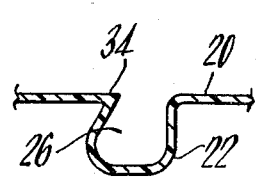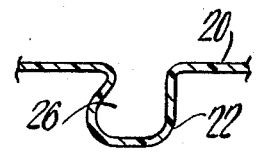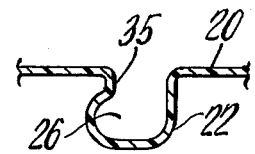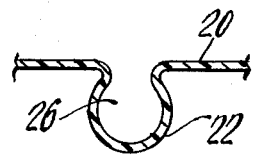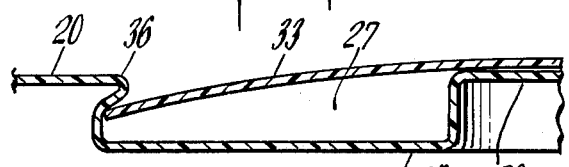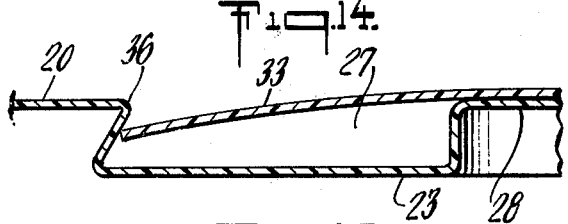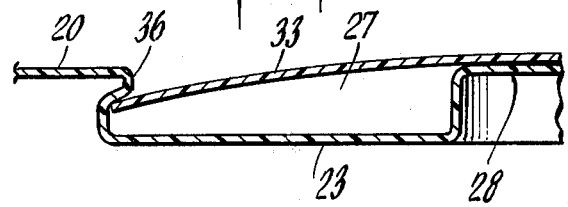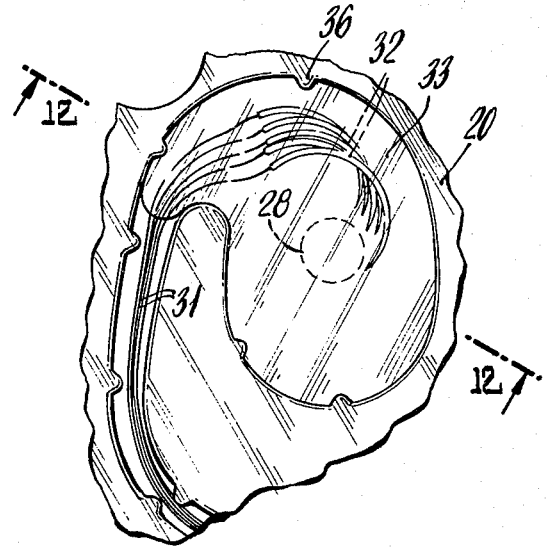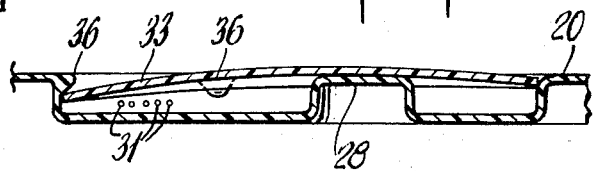

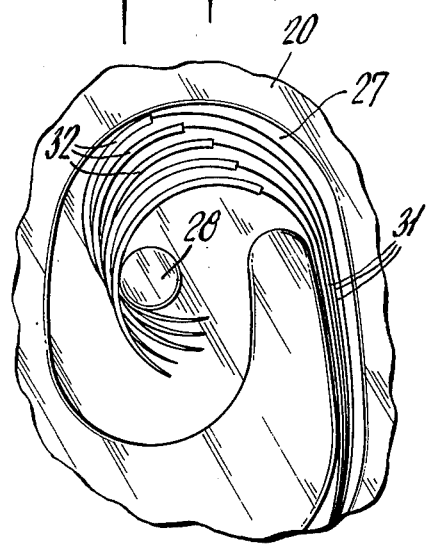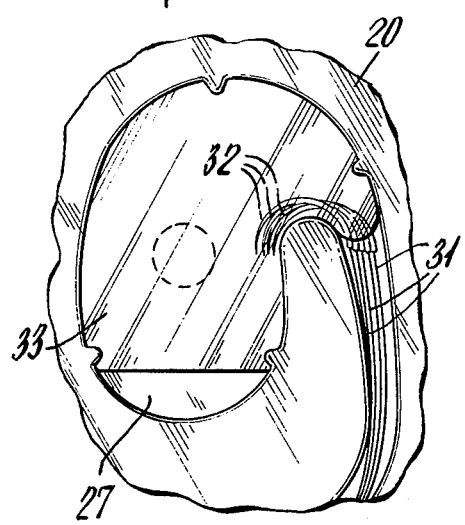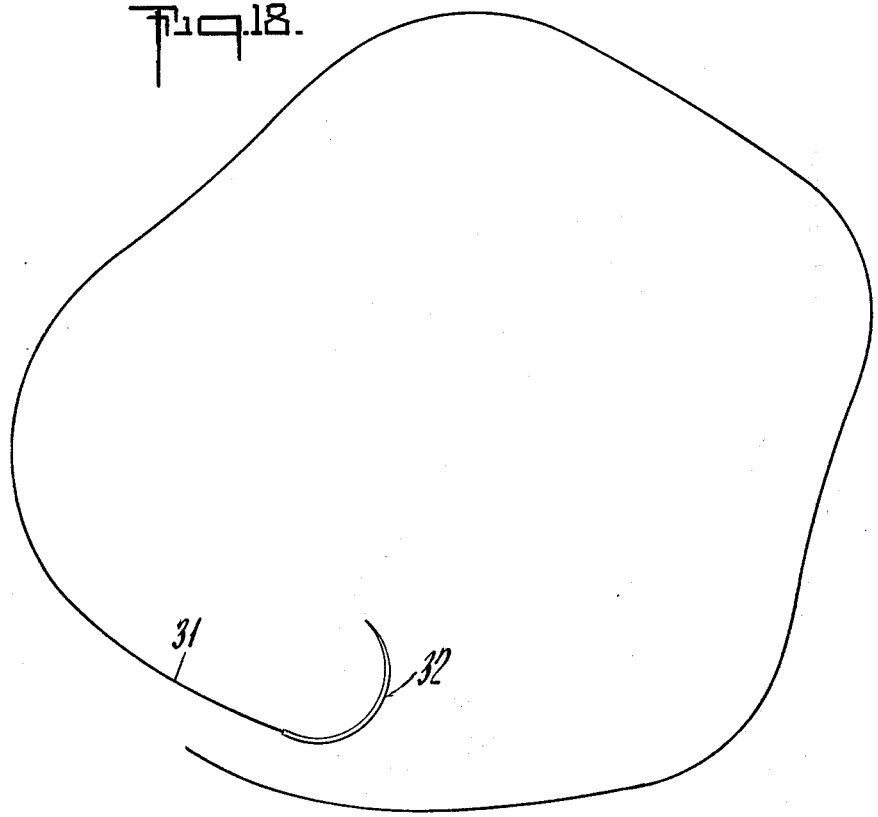

MOLDED SUTURE PACKAGE

BACKGROUND OF THE INVENTION

This invention relates to suture packages, and more particularly to packages which provide for the convenient delivery of monofilament sutures in a substantially uncoiled, unlooped form.

Certain suture materials, particularly monofilaments such as catgut and polypropylene in the heavier deniers, are known to take a "set" during storage, i.e., they retain the shape of their position in the package when removed from the package. For example, when such sutures are looped, wound in the form of a coil or wound upon a reel and stored in such a condition, and suture will set to that configuration and, when removed from the package, will tend to form a number of loops or coils. Such sutures are prone to tangle and are difficult to keep separate when several sutures are being used in a single operation. It has accordingly been necessary for the nurse or surgeon removing such sutures from the package to at least partially straighten the suture by stretching it before it is ready for use.

Molded packages have been suggested for use with sutures heretofore. U.S. Pat. No. 3,338,401 for example, discloses molded laminated packages which are designed to avoid the formation of kinks and sharp bends in delicate flexible sutures. The packages of this reference are characterized by having a needle chamber located at one end of the package and a suture channel having a plurality of rather tight convolutions in the form of a spiral or modified FIG. 8 pattern over the remainder of the package. Such packages are not well suited for packaging heavier denier monofilament sutures since these less flexible sutures tend to tighten up in th convolutions of the suture channel and cannot be withdrawn from the end of the package as may the more delicate and flexible sutures for which the package was designed. This binding of the suture in the suture channel, commonly referred to as a "capstan effect," is avoided by the packages of the instant invention.

The convolutions of the packages of U.S. Pat. No. 3,338,401 impart considerable curvature to sutures which tend to take a set on storage and such sutures form loops, coils, and/or sinusoidal patterns when removed from the package. In accordance with the present invention, sutures which are prone to take a set are packaged in such a way that when removed from the package they will not be significantly looped or coiled. The packages of the present invention are designed to impart minimum curvature to the suture during storage, to provide for the removal of one or more individual sutures from a package containing several sutures, and, in a preferred embodiment, to partially remove some of the curvature during withdrawal of the suture from the package.

SUMMARY

The packages of the present invention comprise a laminate of a first molded sheet and a second cover sheet. The molded sheet defines a narrow suture channel having a plurality of curves circumscribing and terminating at one end in an enlarged recess centrally located in the molded sheet. Single armed sutures are placed in the suture channel with the needles positioned in the enlarged recess. The cover sheet is adhesively applied to the molded sheet and sealed around the periphery of the package and along the edges of the suture channel and needle recess to form a closed suture passageway and needle chamber.

The suture passageway is characterized by having gentle curves and by defining a generally spiral path outward from and around the central needle chamber. In a preferred embodiment, the suture passageway is characterized by having at least one curve in a direction reverse to the general direction of the spiral. The cover sheet is adapted to be partially peeled from the central portion of the molded sheet to gain access to the needle chamber and an adjacent length of suture channel. Sutures are removed singly or in groups from the opened package by drawing the suture through the reverse curve and out through the open suture channel. Once removed, the sutures are characterized by having only gentle curves and no loops or coils.

DESCRIPTION OF DRAWINGS

FIG. 1 is a plan view of a package according to a preferred embodiment of this invention, viewed from the channel side.

FIG. 2 is a cross-sectional view of the package of FIG. 1 along line 2—2.

FIG. 3 is a plan view of the package of FIG. 1 viewed from the covered side with the cover sheet peeled back to expose the needle chamber and the adjacent portion of suture channel. FIG. 3 additionally shows optional needle chamber cover 33 not included in FIG. 1.

FIG. 4 is a view in perspective of the opened suture package with needles and sutures presented for removal.

FIG. 5 is a plan view of a portion of the suture channel showing projections into the channel.

FIG. 6 is a plan view of a portion of a suture channel showing undercutting along curves.

FIG. 7 is a cross-sectional view of a suture channel taken along line 7—7 showing details of a projection in the channel.

FIG. 8 is a cross-sectional view of a suture channel showing details of an alternative projection design.

FIG. 9 is a cross-sectional view of a suture channel taken along line 9—9 showing detail of undercutting along a curve.

FIG. 10 is a cross-sectional view of a suture channel undercut on both sides.

FIG. 11 is a plan view of the needle chamber and chamber cover before the cover sheet is applied.

FIG. 12 is a cross-sectional view of the needle chamber and chamber cover of FIG. 11 along line 12—12.

FIGS. 13 thru 15 are enlarged cross-sectional partial views of the needle chamber and chamber cover of FIG. 12 illustrating the details of various projection designs.

FIGS. 16 and 17 are views of the needle chamber showing alternate needle positions. FIG. 17 additionally shows a modified design of the needle chamber cover.

FIG. 18 is a representation of a typical suture configuration upon removal from a package of the instant invention.

DESCRIPTION OF PREFERRED EMBODIMENTS

Referring to FIGS. 1—4 of the drawings, there is shown a package according to a preferred embodiment of this invention which comprises a laminate of a first molded sheet 20 and a second cover sheet 21. The molded sheet 20 defines a long narrow channel 22 having a plurality of curved sections circumscribing and terminating at one end in centrally located recess 23. Channel 22 is displaced from the normal plane of the molded sheet in a U-shaped cross-section open to one side of the molded sheet. Recess 23 is in a like manner displaced from the normal plane of the molded sheet and open to same side of the molded sheet as the suture channel.

Cover sheet 21 is sealed to molded sheet 20 continuously along both longitudinal edges 24 of channel 22 and rim 25 of recess 23 to form a closed suture channel passageway 26 terminating in a closed needle chamber 27.

In a preferred embodiment, recess 23 is molded with a central plateau 28 extending from the bottom of the recess to the normal plane of the molded sheet. Also in a preferred embodiment, molded sheet 20 has a finger hole 29 providing access to cover sheet 21 at a location where cover sheet 21 is cut or perforated and adapted to be peeled away from the molded sheet. In FIG. 1, the line of the cut or perforations in cover sheet 21 is indicated by dashed line 30.

Turning now to FIG. 3, there is shown a view from the cover sheet side of the package wherein cover sheet 21 has been peeled back from the open side of molded sheet 20 along dashed line 30, thereby exposing needle chamber 27 and a portion of suture channel 26 which contains sutures 31 terminating with needles 32. Also illustrated in FIG. 3 is needle chamber cover 33 which, in a preferred embodiment hereinafter described, is placed over the needle chamber between the molded sheet 20 and cover sheet 21 and is adhered to said cover sheet and removed from the needle chamber when cover sheet is peeled away.

FIG. 4 illustrates the opened package of FIG. 3 inverted to present needles 32 and a length of suture 31 whereby the suture strands may be individually grasped and withdrawn from the package singly or in groups of two or more.

Turning now to FIGS. 5 thru 10, there are illustrated various channel details which may be employed in preferred embodiments of the present invention hereinafter described. In FIG. 5, channel 22 is undercut with a plurality of spaced projections 34 having the cross-section as shown in FIG. 7. In FIG. 6, channel 22 is provided with continuous undercuts 35 along inside curves of the channel having the cross-section shown in FIG. 9. FIG. 8 shows an alternate cross-section for undercut channels which preserves a circular configuration in the channel. The projections or undercutting of FIGS. 7–10 preferably extend into the suture channel a distance equal to at least one-eighth and preferably one-fourth or more of the width of the channel in the normal plane of the molded sheet. Any cross-section of FIGS. 7–10 can be used with the undercutting of either FIGS. 5 or 6, and the undercutting of FIG. 6 may be continuous along either or both sides of the suture channel and over substantially the entire length of the suture channel.

FIGS. 11 and 12 illustrate in detail a needle chamber having a cover 33 positioned over the chamber and restrained between projections 36 and plateau 28. Cover 33 in combination with molded recess 23 thereby defines needle chamber 27 prior to the application of cover sheet 21. Projections 36 may be of any suitable design effective to restrain cover 33 as illustrated for example in FIGS. 13–15 which show partial enlarged views of the covered needle chamber.

FIGS. 16 and 17 are views of the needle chamber illustrating the manner in which needles of various sizes may be accommodated. In FIG. 16. large needles as for example half circle needles having a radius of three-fourth inch or larger are placed with the needle extending around the central plateau 28. Smaller needles, for example half circle needles having a radius of one-half inch or smaller, may be positioned at the juncture of the needle chamber and the suture channel as shown in FIG. 17, or may be extended further into the needle chamber if desired. FIG. 17 additionally illustrates a modified needle chamber cover wherein the lower portion of the cover has been removed. This design is preferred for use with packages containing a tubing fluid to prevent the chamber cover from dipping into and splashing the tubing fluid when opening the package.

The needle-suture combinations may be placed into the packages of the instant invention mechanically or manually using any convenient means. In one method, the molded sheet 20 is placed open side up and one or several armed sutures are manually placed in the open suture channel and needle recess. It is generally most convenient to position the needles in the needle recess first, then lay the sutures in the suture channel, the sutures having been precut to a length corresponding to the length of the suture channel or shorter if desired.

In a preferred embodiment, the needle chamber has a plurality of projections extending from the lip thereof, and a centrally located plateau as shown in FIGS. 11 and 12. After loading the needle-sutures into the recess in the molded sheet, a separate needle chamber cover 33 is snapped into place to hold the needles in position until the cover sheet is applied. Once the needle-suture combinations are loaded into the molded sheet and cover 33 is in place, cover sheet 21 is applied and bonded to the molded sheet by heat sealing or other adhesive means to obtain the laminate structure of FIGS. 1 and 2.

Molded sheet 20 is preferably formed from a transparent plastic material which is capable of being molded by thermoforming injection molding or the like to provide a sharply defined, relatively rigid structure such as shown in FIGS. 1 and 2. In this construction, the bottoms of channel 22 and recess 23 are displaced from the normal plane of sheet 20 and adjacent portions of the channel are separated from the needle recess and from each other by narrow portions of the molded sheet which remain in the original plane of the sheet.

Cover sheet 21 is preferably constructed of a material capable of being peelably sealed to the molded sheet in such a way that the cover sheet and the molded sheet may be readily separated. The cover sheet may comprise a barrier layer of a material such as aluminum foil and an inner heat sealing layer which is adapted to join the cover sheet to the molded sheet, and may include an outer protective layer of a material such as Mylar film.

Any cover sheet which is adapted to be sealed to the exposed portions of the molded sheet and form a sealed unit may be used. The materials used and the sealing techniques applied must be chosen so that the cover sheet may be stripped or peeled from the molded sheet along a precut line without tearing. When it is desired that the molded member and the cover sheet cooperate to form a hermetically sealed package for a sterile suture, they must be selected from sheet materials, such as those described above, which will provide the necessary barriers to the passage of bacteria and which are capable of being sterilized in a conventional manner by either irradiation, gaseous diffusion, heat, or the like without serious deterioration or loss of desired properties. The packages of this invention are particularly suited for forming hermetically sealed units because they are adapted to be filled easily and sealed safely and then to be opened by peeling the cover sheet from the package without danger of contaminating its sterile contents.

The composition and fabrication of the packages of the instant invention are in accordance with known technology as described for example in U.S. Pat. No. 3,338,401, which patent is hereby incorporated herein by reference for its teachings in this regard.

While any composition or fabrication of needle-suture combinations may be used in the novel package of the instant invention, the packages are particularly well adapted for use with heavy monofilament suture materials which tend to take a "set" when stored over extended periods of time. In particular, collagen sutures, including both catgut and extruded collagen, and synthetic monofilament sutures of polypropylene, nylon and polyesters in sizes of 4–0 and larger, particularly sizes 1–0 and larger, are known to take a set during storage. The packages of the instant invention provide for the relatively straight delivery of such sutures. By "straight delivery" it is not meant that the delivered suture is perfectly linear in form, but rather that the suture is delivered with only gentle bends and without any pronounced loops or coils whereby it is suitable for use with little or no straightening. It is a critical feature of the instant invention that the needle-chamber is centrally located, and that the suture is laid circumferentially around the needle-chamber in a generally spiral pattern whereby the number and severity of curves in the suture channel are minimized. It is a preferred feature of the instant invention that the suture channel has at least one curve in a reverse direction from the primary direction of the spiral. Referring to FIG. 1, the suture channel defines a spiral having a clockwise direction around the central needle chamber, and reverse curvature is present at points A and B in this illustration. Reverse curvature in the suture channel works to straighten the suture as it is pulled through the curve upon withdrawal from the package. Reverse curve A in FIG. 1 tends to straighten the set imparted to the suture in the two final curves of the spiral, while reverse curve B tends to straighten the set imparted to the suture over the entire length of the spiral between point B and the end of the suture. The reverse curvature also imparts a small degree of reverse set in the suture which tends to open the suture spiral upon delivery from the package. With reference to FIG. 18, there is illustrated a typical size 0 polypropylene monofilament suture as it appears upon delivery from the suture package of FIG. 1 without the application of any additional straightening efforts. It is most significant that, as illustrated in FIG. 18, there are no loops or coils in the suture, nor does it cross at any point, and a suture having such a low degree of curvature is useable with little or no additional straightening.

The suture package of the present invention has several convenience features hereinbefore described with reference to the Figures. Specifically, the suture channel is optionally equipped with a plurality of projections as illustrated in FIGS. 5 and 7 through 10. Projections such as those of FIG. 7 reduce the cross-sectional area of the suture channel and, when located in the reverse curves of the suture channel, increase the drag on the suture as it is drawn through these curves to enhance the straightening effect of the reverse curve. In one embodiment of the present invention, the reverse curve has at least two generally opposing projections within the curve as shown for example in FIG. 5. Additionally, projections such as those illustrated in FIGS. 7 thru 10 which undercut the channel opening serve to hold the suture in the channel during the loading and covering operations. The continuous undercuts illustrated in FIG. 6 like-wise facilitate loading and covering the suture package by restraining the suture strands within the channel.

With further reference to FIG. 1, finger hole 29 is optionally provided to push the tear end of the cover sheet away from the molded sheet whereby it is readily grasped and the cover sheet peeled back from the molded sheet along line 30 which is a cut or perforated line in the cover sheet. To facilitate opening of the package without tearing the cover sheet, a narrow portion of the cover sheet along either side of the precut line is preferably not sealed to the molded sheet. Other means to gain access to the central needle chamber will be apparent to those skilled in the packaging art.

It is preferred that the cover sheet be cut or perforated along lines substantially traversing the suture package in order that when the cover sheet is peeled from the molded sheet, a substantial length of suture channel is uncovered along with the needle chamber as shown in FIGS. 3 and 4. Opening a portion of the suture channel allows the needles to be presented with a length of suture available for grasping. This is particularly important when the package contains controlled release suture, i.e., needle-suture combinations manufactured so that the needle may be pulled off the suture with a force of from about 3 to 26 ounces. Should a nurse or surgeon attempt to remove such a controlled release suture from the package by grasping the needle, the needle might prematurely release from the suture.

Another advantage to partially opening the suture channel is that the suture does not have to be drawn through the final curvature leading to the needle chamber. This reduces the tendency of some suture materials, particularly the heavier denier monofilament sutures to tighten up in the suture channel as they are being withdrawn, a tendency which may be described as a capstan effect caused by the suture frictionally engaging the walls of the channel. We have found that there is little or no capstan effect experienced when the sutures are withdrawn from the channel at point C in FIG. 4 after the cover sheet is peeled back the full length of the cut portion.

The invention has been described herein in terms of detail associated with preferred embodiments thereof. It will be readily apparent to those skilled in the art that innumerable variations, applications, modifications and extensions of the basic principles embodied in the invention may be made without departing from the spirit or scope thereof. The packages may, for example, include a fluid chamber connected to the suture passageways and means for introducing a fluid into the chamber and passageways when the suture of the package is preferably stored in a tubing fluid. Packages for smaller denier sutures may be equipped with means for vacuum loading the sutures into the package. The packages may additionally be used with unarmed sutures if desired. Many of these and other optional features are described in U.S. Pat. No. 3,338,401, and yet other variations will be apparent to those skilled in the art.

What is claimed is:

1. In a package for armed sutures comprising a laminate of a first molded sheet and a second cover sheet, said molded sheet defining an elongated suture channel terminating at one end in an enlarged needle chamber, said channel and said chamber having a bottom and side walls, said bottom being displaced from the normal plane of the molded sheet and said side walls extending from said bottom to said normal plane of the molded sheet, said channel and said chamber being open to one side of the molded sheet, said cover sheet being flat and sealed to said molded sheet along the open side of said channel and said chamber to close said channel and said chamber and form a closed suture channel terminating at one end in a closed needle chamber, the improvement comprising locating the needle chamber centrally of the package, extending the suture channel in a path circumscribing said needle chamber, and precutting the cover sheet along a line intermediate the needle chamber and adjacent convolutions of the suture channel whereby a portion of the cover sheet is adapted to be opened to provide access to the needle chamber.

2. A package of claim 1 wherein the suture channel defines a spiral circumscribing said needle chamber.

3. A package of claim 2 wherein the suture channel has at least one curve in a reverse direction from the primary direction of said spiral.

4. A package of claim 1 wherein a narrow portion of the cover sheet along either side of said precut line is not sealed to said molded sheet.

5. A package of claim 1 wherein the molded sheet has a hole opposite that portion of the cover sheet adapted to be opened and adjacent said precut line in said cover sheet.

6. In a package for armed sutures comprising a laminate of a first molded sheet and a second cover sheet, said molded sheet defining an elongated suture channel terminating at one end of an enlarged needle chamber, said channel and said chamber having a bottom and side walls, said bottom being displaced from the normal plane of the molded sheet and said side walls extending from said bottom to said normal plane of the molded sheet, said channel and said chamber being open to one side of the molded sheet, said cover sheet being flat and sealed to said molded sheet along the open side of said channel and said chamber to close said channel and said chamber and form a closed suture channel terminating at one end in a closed needle chamber the improvement comprising locating the needle chamber centrally of the package, providing said needle chamber with a centrally located plateau extending from the bottom of the chamber to the normal plane of the molded sheet, and extending the suture channel from the needle chamber in a path circumscribing said needle chamber.

7. In a package for armed sutures comprising a laminate of a first molded sheet and a second cover sheet, said molded sheet defining an elongated suture channel terminating at one end in an enlarged needle chamber, said channel and said chamber having a bottom and side walls, said bottom being displaced from the normal plane of the molded sheet and said side walls extending from said bottom to said normal plane of the molded sheet, said channel and said chamber being open to one side of the molded sheet, said cover sheet being flat and sealed to said molded sheet along the open side of said channel and said chamber to close said channel and said chamber and form a closed suture channel terminating at one end in a closed needle chamber, the improvement comprising locating the needle chamber centrally of the package, extending the suture channel in a path circumscribing said needle chamber, interrupting the continuity of the sidewalls of said suture channel by a pluralitiy of projections extending into said channel from the walls thereof.

8. A package of claim 7 wherein said projections extend into said channel for a distance of at least one-eighth the width of said channel in the normal plane of the molded film.

9. A package of claim 7 wherein the suture channel defines a spiral circumscribing said needle chamber and said channel has at least one curve in a reverse direction from the primary direction of said spiral.

10. A package of claim 9 wherein said projections reduce the cross-sectional area of the suture channel in said reverse curve.

11. A package of claim 10 wherein said reverse curve has at least two projections extending from opposite walls of the channel.

12. A package of claim 7 wherein the continuity of the walls of the needle chamber are interrupted by a plurality of projections extending into the chamber from the walls thereof.

13. A package of claim 12 wherein said projections extend into said channel and said chamber for a distance of at least one-eighth the width of said channel in the normal plane of the molded film.

14. A package of claim 13 wherein the needle chamber has a centrally located plateau extending from the bottom of the chamber to the normal plane of the molded sheet, and a chamber cover held in place within the walls of said chamber by engagement between said projections and said central plateau.

15. In a package for armed sutures comprising a laminate of a fist molded sheet and a second cover sheet, said molded sheet defining as elongated suture channel terminating at one end is an enlarged needle chamber, said channel and said chamber having a bottom and side walls, said botom being displaced from the normal plane of the molded sheet and said side walls extending from said bottom to said normal plane of the molded sheet, said channel and said chamber being open to one side of the molded sheet, said cover sheet being flat and sealed to said molded sheet along the open side of said channel and said chamber to close said channel and said chamber and form a closed suture channel terminating at one end in a closed needle chamber, the improvement comprising locating the needle chamber centrally of the package, extending the suture channel in a path circumscribing said needle chamber, and undercutting the sidewalls of said suture channel in the curves to reduce the width of the channel opening in the plane of the molded sheet in said curves.

16. A package of claim 15 wherein the inside curves of said side walls are undercut.

* * * * *

UNITED STATES PATENT AND TRADEMARK OFFICE
CERTIFICATE OF CORRECTION

PATENT NO. : 3,972,418
DATED : August 3, 1976
INVENTOR(S) : Schuler, Michael et al It is certified that error appears in the above-identified patent and that said Letters Patent are hereby corrected as shown below:

Asst. Examiner: "Bruce H. Bernstel" should read --- Bruce H. Bernstein ---.

In Column 1, line 15, the word "such a condition, and" should read --- such a condition, the ---.

In Claim 6, line 44, the word "of an enlarged" should read --- in an enlarged ---.

In Claim 15, line 45, the word "fist should read --- --- first ---.

In Claim 15, line 46, the word "as" should read --- an ---.

In Claim 15, line 47, the word "is" should read --- in ---.

In Claim 15, line 49, the word "botom" should read --- bottom ---.

Signed and Sealed this

Eighteenth Day of October 1977

[SEAL]

Attest:

RUTH C. MASON
Attesting Officer

LUTRELLE F. PARKER
Acting Commissioner of Patents and Trademark